United States Patent [19]

Koppe et al.

[11] 3,940,489
[45] Feb. 24, 1976

[54] THERAPEUTIC COMPOSITIONS AND METHOD

[75] Inventors: Herbert Koppe, Ingelheim am Rhein; Albrecht Engelhardt, Mainz (Rhine); Karl Zeile, Ingelheim am Rhein, all of Germany

[73] Assignee: Boehringer Ingelheim GmbH, Ingelheim am Rhein, Germany

[22] Filed: Sept. 3, 1974

[21] Appl. No.: 502,634

Related U.S. Application Data

[60] Division of Ser. No. 408,743, Oct. 23, 1973, Pat. No. 3,868,460, which is a division of Ser. No. 294,226, Oct. 2, 1972, which is a division of Ser. No. 36,676, May 12, 1970, Pat. No. 3,740,444, which is a continuation-in-part of Ser. No. 700,376, Jan. 25, 1968, Pat. No. 3,541,130.

[30] Foreign Application Priority Data

June 15, 1967 United Kingdom............... 27645/67
July 25, 1967 Germany................................. 93645
Feb. 6, 1967 Germany................................. 91070
June 15, 1967 Germany................................. 93025

[52] U.S. Cl. .............................................. 424/309
[51] Int. Cl.² ........................................... A61K 31/24
[58] Field of Search .................................. 424/309

[56] References Cited
OTHER PUBLICATIONS

Sohn – Chem. Abst. Vol. 68 (1968) p. 68689r.

*Primary Examiner*—Sam Rosen
*Attorney, Agent, or Firm*—Hammond & Littell

[57] ABSTRACT

A composition having bradycardia and isoproterenol antagonistic activity comprising at least one compound selected from the group consisting of racemates of 1-phenoxy-2-hydroxy-3-tert.-butylamino propanes of the formula

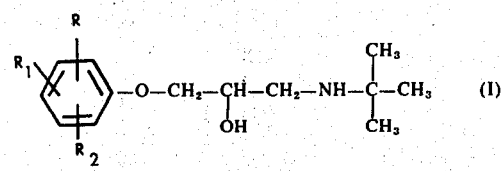

wherein R is selected from the group consisting of $-(CH_2)_x-CH$ where $x$ is an integer from 0 to 3, COOH and COOR' where R' is alkyl of 1 to 4 carbon atoms; $R_1$ is selected from the group consisting of hydrogen, alkoxy and alkylthio of 1 to 4 carbon atoms, $-CH$ and alkenyl and alkynyl of 2 to 4 carbon atoms and $R_2$ is selected from the group consisting of hydrogen, halogen and alkyl and alkoxy of 1 to 4 carbon atoms, their optically active isomers and their non-toxic, pharmaceutically acceptable acid addition salts of said racemates and said optically active isomers and a major amount of a pharmaceutical carrier and a method of producing bradycardia and suppressing tachycardia effects of N-isopropyl-noradrenaline in warm-blooded animals.

10 Claims, No Drawings

THERAPEUTIC COMPOSITIONS AND METHOD

PRIOR APPLICATION

This application is a division of our copending application Ser. No. 408,743 filed Oct. 23, 1973, now U.S. Pat. No. 3,868,460 which is a division of application Ser. No. 294,226 filed Oct. 2, 1972, which in turn is a divisional application of our copending application Ser. No. 36,676 filed May 12, 1970, now U.S. Pat. No. 3,740,444, which in turn is a continuation-in-part application of our copending commonly-assigned U.S. Pat. applicaton Ser. No. 700,376 filed Jan. 25, 1968, now U.S. Pat. No. 3,541,130.

OBJECTS OF THE INVENTION

It is an object of the invention to provide novel compositions having bradycardia and isoproterenol activity.

It is another object of the invention to provide a novel method of inducing bradycardia and isoproterenol-antagonistic activity in warm-blooded animals.

These and other objects and advantages of the invention will become obvious from the following detailed description.

THE INVENTION

The novel compositions of the invention having bradycardia and isoproterenol antagonistic activity are comprised of at least one compound selected from the group consisting of racemates of 1-phenoxy-2-hydroxy-3-tert.-butylamino propanes of the formula

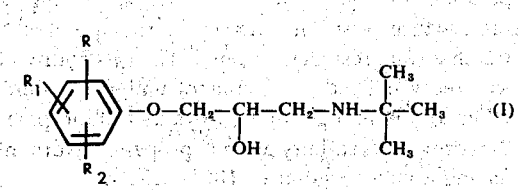

wherein R is selected from the group consisting of $-(CH_2)_x$, $-CN$ and $-(CH_2)_x-NH_2$ where x is an integer from 0 to 3, COOH and COOR' where R' is alkyl of 1 to 4 carbon atoms; $R_1$ is selected from the group consisting of hydrogen, alkoxy and alkylthio of 1 to 4 carbon atoms, $-CN$ and alkenyl and alkynyl of 2 to 4 carbon atoms and $R_2$ is selected from the group consisting of hydrogen, halogen and alkyl and alkoxy of 1 to 4 carbon atoms, their optically active isomers and their non-toxic, pharmaceutically acceptable acid addition salts of said racemates and said optically active isomers and a major amount of a pharmaceutical carrier.

Examples of non-toxic, pharmacologically acceptable acids suitable for addition salts are inorganic acids such as hydrochloric acid, hydrobromic acid, sulfuric acid, phosphoric acid and organic acids such as methane sulfonic acid, acetic acid, lactic acid, tartaric acid, ascorbic acid, 8-chlorotheophylline and the like.

The compounds according to the present invention may be prepared by a number of different methods involving known chemical reaction principles; however, among these, the following methods have been found to be most convenient and efficient:

METHOD A

By reacting an epoxide of the formula

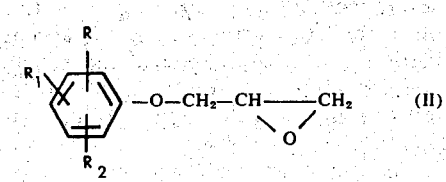

where the R's have the same meanings as in formula I, with tert.-butylamine in the presence of an inert organic solvent, such as ethanol.

METHOD B

By reacting a 1-substituted phenoxy-2-hydroxy-3-halopropane of the formula

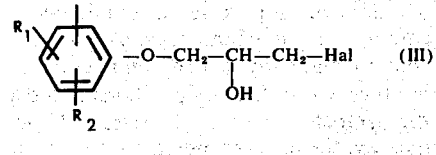

wherein the R's have the same meanings as in formula I and Hal is halogen, with tert.-butylamine in the presence of an inert organic solvent, such as ethanol.

The starting compounds of the formula II to III for the above methods are known compounds or may readily be prepared by known methods. For example, the substituted 1-phenoxy-2,3-epoxy propanes of formula II may be prepared by reacting a corresponding substituted phenolate under alkaline conditions with a 1-halo-2,3-epoxy propane such as epichlorohydrin. Most of the corresponding phenols are known in the prior art and they are easily obtainable by conventional methods. Cyanophenols, particularly those with alkyl and/or alkoxy groups, may be prepared by splitting off water from the correspondingly substituted phenolic benzaldoximes which are prepared from known phenolic benzaldehydes. Cyanophenols with an allyl substituent are obtained by reacting the cyanophenol with allyl bromide with rearrangement of the intermediate allyl ether into the final product. Halocyanophenols are obtained by reacting the cyanophenol with a hydrogen halide in the presence of $H_2O_2$. Cyanomethylphenols can be made by introducing a nitro group into a benzylnitrile and converting it into a phenol group by reducing, diazotizing and boiling down. The aminoalkyl substituted compounds of formula I are prepared by reduction of the corresponding cyano or cyanoalkyl substituted compounds, which in turn can be obtained by method A.

The amino-substituted compounds of formula I are prepared by reacting the corresponding nitrophenols with epichlorohydrin to form the corresponding 2,3-epoxy compound which is reacted with tert.-butylamine and then the nitro group is reduced to the amino group. Other processes are described in Belgian Pat. No. 641,133 and in the literature.

The free bases of formula I obtained by any of the above methods may subsequently be transformed into their nontoxic, pharmacologically acceptable acid addition salts by conventional methods, that is, by acidifying a solution of the free base with the desired acid and recovering the acid addition salt by evaporation of the solvent or by precipitation, for instance.

The compounds of the formula I possess on the —CHOH-grouping an asymmetric C-atom, and consequently, occur in the form of racemates as well as in the form of optically active antipodes.

The optically active compounds can be obtained in that one proceeds either from optically active starting compounds or that the racemates obtained are split into their optical antipodes in the usual manner, for example, by means of dibenzoyl-D-tartaric acid or D-3-bromocamphor-8-sulfonic acid or di-p-toloyl-d-tartaric acid.

The said compositions of the invention produce bradycardia and at the same time act as N-isopropyl-noradrenaline (Isoproterenol) antagonists as shown in dogs and guinea pigs. Thus, the tachycardiac effects caused by the administration of N-isopropyl-nora-drenaline are suppressed or eliminated by prior administration of one of the compositions of the present invention, and cardiac arrhythmia are equalized by them. In other words, the compositions of the invention block the sympathetic nervous system of the heart. Consequently, the areas of indication for the compositions, of the present invention are hypertension, angina pectoris, cardiac arrhythmia, digitalis intoxication and pheochromocytoma disorders. They may also be used in conjunction with coronary dilator or sympathicomimetic agents. The compositions may be in the form of injectable solutions or suspensions, tablets, dragees, sustained release tablets, etc. The usual dose is 1 to 300 mg, preferably 1 to 150 mg, for oral administration and 1 to 20 mg for parental administration.

The novel method of the invention of inducing bradycardia and of suppressing tachycardiac effects of N-isopropylnoradrenaline in warm-blooded animals comprises administering to warm-blooded animals a safe and effective amount of at least one of the compounds of formula I. The said compounds may be administered orally, parentally or rectally. The usual dosage is 0.002 to 5 mg/kg, depending upon the method of administration.

In the following examples there are described several preferred embodiments to illustrate the invention. However, it should be understood that the invention is not intended to be limited to the specific embodiments.

EXAMPLE I

Preparation of
1-(2-cyano-3-methyl-phenoxy)-2-hydroxy-3-tert.-butylamino propane. HCl 1-(2-cyano-3-methyl-phenoxy)-2,3-epoxy propane, prepared from 17 gm (0.128 mol) of 2-cyano-3-methylphenol and 12.2 gm (0.132 mol) of epichlorohydrin in 125 ml of 1 N NaOH, was dissolved as a dark, impure viscous oil in 200 ml of methanol, and 29 ml of tert.-butylamine were added thereto. After refluxing the mixture for 2 hours, the solvent was distilled off under vacuum, and the brown residue was extracted with dilute HCl. The clear solution was filtered over charcoal and was made alkaline with NaOH. The precipitating base was taken up in ether and the organic phase was separated and was washed repeatedly with water and dried over MgSO$_4$. After concentration up to weight constancy, 4.5 gm of a base remained and this was dissolved in a small amount of ethanol. The hydrochloride salt was precipitated by an addition of ethereal HCl and was isolated as a solid product. It was recrystallized from acetonitrile with an addition of ether followed by a second recrystallization from ethanol with an addition of ether to obtain 1-(2-cyano-3-methyl-phenoxy)-2-hydroxy-3-tert.-butylamino propane hydrochloride having a melting point of 178° – 180°C. Using this same procedure, there was obtained 1-(2-cyanomethyl-3-methyl-phenoxy)-2-hydroxy-3-tert.-butylamino-propane hydrochloride.

EXAMPLE II

Preparation of
1-(2-cyano-4-chlorophenoxy)-2-hydroxy-3-tert.-butylamino propane. HCl 5.7 gm (0.02 mol) of 1-(2-cyanophenoxy)-2-hydroxy-3-tert.-butylamino propane (prepared analogous to Example I) were dissolved in 32 ml of concentrated HCl and while stirring at 45° C, 2.27 gm of 35% hydrogen peroxide were added dropwise so that the temperature did not exceed 65°C. Thereafter, the temperature was maintained at 60°C for 30 minutes and the mixture was concentrated in vacuo at the end of which a solid residue remained. The raw hydrochloride was recrystallized from ethanol under an addition of ether to obtain 3 gm of 1-(2-cyano-4-chlorophenoxy)-2-hydroxy-3-tert.-butylamino propane hydrochloride having a melting point of 180° – 182°C.

EXAMPLE III

Preparation of
1-(2-methyl-4-cyanophenoxy)-2-hydroxy-3-tert.-butylamino propane. HCl 24 gm of 1-(2-methyl-4-cyanophenoxy)-2,3-epoxy-propane in 150 ml of ethanol were reacted with 25 ml of tert.-butylamine. After refluxing the reaction mixture for 2 hours, the solvent was distilled off in vacuo, and the residue was dissolved in dilute HCl. After extraction with ether, the aqueous phase was made alkaline with NaOH and the precipitated base was taken up in ether. The ether solution was washed with H$_2$O, dried over MgSO$_4$, and finally the ether was distilled off. The residue was dissolved in 100 ml of ethanol and ethereal HCl was added thereto. The precipitating crystalline hydrochloride was isolated and recrystallized from methanol with an addition of ether to obtain 17 gm of pure 1-(2-methyl-4-cyanophenoxy)-2-hydroxy-3-tert.-butylamino propane hydrochloride having a melting point of 230° – 231°C.

EXAMPLE IV

Preparation of 1-(2-methoxy-4-cyanophenoxy)-2-hydroxy-3-tert.-butylamino propane. HCl 9.9 gm (0.048 mol) of 1-(2-methoxy-4-cyanophenoxy)-2,3-epoxy propane in 100 ml of ethanol were heated with 14.6 gm (0.02 mol; 21 ml) of tert.-butylamine for 3 hours over a water bath. After distillation of the solution in vacuo, the residue was digested with dilute HCl and the solution was separated from the insoluble matter. The aqueous phase was made alkaline with NaOH and the precipitated base was extracted with ether, washed with water, and the organic phase was dried over MgSO$_4$. After distilling off the ether, the oily residue was dissolved in ethanol, admixed with ethereal HCl, and the precipitating crystals of 1-(2-methoxy-4-cyanophenoxy)-2-hydroxy-3-tert.-butylamino propane hydrochloride were vacuum filtered and recrystallized from ethanol with an addition of ether to obtain 7.1 gm of the product having a melting point of 210° – 213°C.

EXAMPLE V

Preparation of 1-(2-aminomethyl-4-chlorophenoxy)-2-hydroxy-3-tert.-butylamino propane. 2 HCl 6.3 gm (0.02 mol) of 1-(2-cyano-4-chlorophenoxy)-2-hydroxy-3-tert.-butylamino propane hydrochloride were dissolved in 100 ml of methanol containing 10 ml of NH$_3$ and the mixture was hydrogenated under normal pressure at 20°C over Raney-nickel. After separation of the catalyst, the solvent was distilled off in vacuo, and the residue was admixed with ether and water. After an addition of a small amount of NaOH, the aqueous phase was separated and the organic phase was washed with water and dried over MgSO$_4$. After distilling off the ether, a solid residue remained which was recrystallized from ethyl acetate with an addition of petroleum ether to obtain 1-(2-aminomethyl-4-chlorophenoxy)-2-hydroxy-3-tert.-butylamino propane. The base was dissolved in ethanol and ethereal HCl was added thereto. The precipitated crystals of the hydrochloride of the base were isolated to obtain 3.1 gm of the hydrochloride having a melting point of 118° – 120°C.

EXAMPLE VI

Using the procedure of Example V, 1(2-methoxy-4-cyanophenoxy)-2-hydroxy-3-tert.-butylamino propane hydrochloride was hydrogenated to form 1-(2-methoxy-4-aminomethylphenoxy)-2-hydroxy-3-tert.-butylamino propane dihydrochloride having a melting point of 235° – 238°C.

EXAMPLE VII

Using the procedure of Example V, 1-(2-cyanophenoxy)-2-hydroxy-3-tert.-butylamino propane hydrochloride was hydrogenated to obtain 1-(2-aminomethyl-phenoxy)-2-hydroxy-3-tert.-butylamino propane dihydrochloride having a melting point of 220° – 222°C.

EXAMPLE VIII

Using the procedure of Example IV, 1-(2-methoxycarbonylphenoxy)-2,3-epoxy-propane was reacted with tert.-butylamine to form 1-(2-methoxycarbonylphenoxy)-2-hydroxy-3-tert.-butylamino propane hydrochloride having a melting point of 144° – 146°C.

EXAMPLE IX

By saponification of 1-(2-methoxycarbonylphenoxy)-2-hydroxy-3-tert.-butylamino propane with sodium hydroxide, there was obtained 1-(2-hydroxycarbonylphenoxy)-2-hydroxy-3-tert.-butylamino propane hydrochloride having a melting point of 138° –140°C.

EXAMPLE X

Using the procedure of Example IV, tert.-butylamine and 1-(2-methoxy-5-cyanophenoxy)-2,3-epoxy propane were reacted to obtain 1-(2-methoxy-5-cyanophenoxy)-2-hydroxy-3-tert.-butylamino propane hydrochloride having a melting point of 149° – 152°C.

EXAMPLE XI

Using the procedure of Example IV, tert.-butylamine and 1-(4-methoxycarbonylphenoxy)-2,3-epoxy propane were reacted to form 1-(4-methoxycarbonylphenoxy)-2-hydroxy-3-tert.-butylamino propane hydrochloride having a melting point of 205° – 207°C.

EXAMPLE XII 1-(4-methoxycarbonylphenoxy)-2-hydroxy-3-tert.-butylamino propane was chlorinated analogous to Example II to obtain 1-(2-chloro-4-methoxycarbonylphenoxy)-2-hydroxy-3-tert.-butylamino propane hydrochloride having a melting point of 208° – 210°C.

EXAMPLE XIII

Preparation of 1-(2-cyanophenoxy)-2-hydroxy-3-tert.-butylamino propane. HCl 15 gm (0.085 mol) of 1-(2-cyanophenoxy)-2,3-epoxy propane were dissolved in 100 ml of ethanol and 18.6 gm (0.255 mol) of tert. -butylamine were added thereto. After standing for 1 hour at room temperature, the solution was heated at 60° – 70°C for 2 hours after which the volatile constitutents were distilled off in vacuo. The residue was digested with dilute HCl, and the insoluble constituents were vacuum filtered off. Then the filtrate was made alkaline with NaOH and the precipitating base was taken up in ether. After the ether solution had been dried over MgSO$_4$, the ether was distilled off and the residue was dissolved in ethanol and by addition of ethereal HCl, the hydrchloride was precipitated therefrom in crystalline form which after recrystallization from ethanol with an addition of ether gave 9.8 gm of 1-(2-cyanophenoxy)-2-hydroxy-3-tert.-butylamino propane hydrochloride having a melting point of 163° – 165°C.

EXAMPLE XIV

Preparation of 1-(4-cyanophenoxy)-2-hydroxy-3-tert.-butylamino propane. HCl 5.7 gm (0.02 mol) of 3-tert.-butyl-5-(4-cyanophenoxymethyl)-oxazolidinone-(2) were dissolved in 50 ml of ethanol. After addition of a solution of 10 gm of potassium hydroxide in 15 ml of water, the solution was refluxed for 2 hours and then the ethanol was distilled off in vacuo, and the residue was extracted with ether. The ethereal phase was separated, dried over MgSO$_4$, and the MgSO$_4$ was filtered off. After concentration of the ether solution, the solid raw base was recrystallized from ethyl acetate to obtain a product having a melting point of 100° – 105°C. After dissolving the crystalline base in ethanol, ethereal hydrochloric acid was added and the solid was isolated and again recrystallized from ethanol/ether to obtain 1.9 gm of 1-(4-cyanophenoxy)-2-hydroxy-3-tert.-butylamino propane hydrochloride having a melting point of 187° – 189°C.

EXAMPLE XV

Preparation of 1-(3-cyanophenoxy)-2-hydroxy-3-tert.-butylamino-2-propane oxalate 9.6 gm (0.05 mol) of 1-(3-cyanophenoxy)-2-hydroxy-3-amino propane were dissolved in 40 ml of dimethylformamide and 100 ml of tetrahydrofuran and 4.2 gm (0.05 mol) of pulverized sodium bicarbonate were added thereto. Then, 6.9 gm (0.05 mol) of tert.-butylbromide were added and the mixture was refluxed for 24 hours. After the mixture had been cooled, the inorganic solid was filtered off and the solvent mixture was distilled off in vacuo. The residue was dissolved by heating in ethyl acetate and the insoluble inorganic portions were vacuum filtered off and the filtrate was admixed with petroleum ether. The base precipitated in solid form and was isolated and recrystallized from ethyl acetate with an addition of petroleum ether to obtain 1-(3-cyanophenoxy)-2-hydroxy-3-tert.-butylamino propane having a melting point of 108° – 110°C.

After having been dissolved in ether, the said product was admixed with an ethereal oxalic acid solution whereby the oxalate precipitated in amorphous form. It was isolated, dissolved in a small amount of ethanol and slowly ether was added thereto. 2.7 gm of the oxalate salt occurred in colorless crystalline form and after being vacuum filtered and dried, melted at 154° – 157°C under decomposition.

EXAMPLE XVI 1-(2-nitro-4-chlorophenoxy)-2-hydroxy-3-tert.-butylamino propane was hydrogenated in the presence of Raney-nickel in methanol to obtain 1-(2-amino-4-chlorophenoxy)-2-hydroxy-3-tert.-butylamino propane dihydrochloride having a melting point of 260° – 262°C.

Using the same procedure of hydrogenation, there were obtained 1-(2-amino-4-fluorophenoxy)-2-hydroxy-3-tert.-butylamino-propane dihydrochloride and 1-(2-nitro-4-bromophenoxy)-2-hydroxy-3-tert.-butylamino propane dihydrochloride.

EXAMPLE XVII

Preparation of 1-(2,4-dichloro-3-aminophenoxy)-2-hydroxy-3-tert.-butylamino-propane. HCl 8.05 gm of 1-(3-nitrophenoxy)-2-hydroxy-3-tert.-butylamino-propane were dissolved in 100 cc of concentrated hydrochloric acid with stirring and the resulting solution was heated to 45°C. Then, 11.3 gm (0.1 mol) of 30% hydrogen peroxide solution were added dropwise while holding the temperature between 50° and 60°C with stirring. After 30 minutes, an oil separated and excess hydrochloric acid was distilled off in vacuo. The residue was taken up in water and the mixture was made alkaline with sodium hydroxide. The resulting free base precipitated as an oil and was dissolved in ethyl acetate. The said solution was washed with water, dried and evaporated to dryness to obtain 9.2 gm (0.0273 mol) of 1-(2,4-dichloro-3-nitrophenoxy)-2-hydroxy-3-tert.-butylamino-propane.

The 9.2 gm of the said base were dissolved in 150 cc of methanol and the said base was hydrogenated in the presence of a Raney-nickel catalyst at room temperature and normal pressure until the theoretical amount of hydrogen (1,240 cc) was adsorbed (2½ hours). The catalyst was then removed by suction filtration and the solvent was distilled off in vacuo. The residue was dissolved in ethanol and the resulting solution was acidified with etherified hydrochloric acid and extracted with ether. After standing in the cold, the dihydrochloride of 1-(2,4-dichloro-3-amino-phenoxy)-2-hydroxy-3-tert.-butylamino-propane crystallized out. After recrystallization twice from acetonitrile, there was obtained 2.5 gm of the dihydrochloride melting at 166° – 169°C.

PHARMACEUTICAL EXAMPLES

| EXAMPLE A - TABLETS | gm |
|---|---|
| 1. 1-(2-cyano-3-methyl-phenoxy)-2-hydroxy-3-tert.-butylamino propane hydrochloride | 40.0 |
| corn starch | 164.0 |
| potassium phosphate | 240.0 |
| magnesium stearate | 1.0 |
| | 445.0 |
| 2. 1-(2-cyano-3-methyl-phenoxy)-2-hydroxy-3-tert,-butylamino propane hydrochloride | 50.0 |
| 2,6-bis-(diethanolamino)-4,8-dipiperidino-pyrimido-[5,4-d]-pyrimidine | 75.0 |
| lactose | 164.0 |
| corn starch | 194.0 |
| colloidal silicic acid | 14.0 |
| polyvinylpyrrolidone | 6.0 |
| magnesium stearate | 2.0 |
| soluble starch | 10.0 |
| | 515.0 |

The individual components are intensively admixed and the mixture is granulated in the usual manner. The granulate is compressed into 1,000 tablets of 500 mg, 445 or 515 mg.

| EXAMPLE B - GELATIN CAPSULES | |
|---|---|
| | mg. |
| 1-(2-cyano-4-chlorophenoxy)-2-hydroxy-3-tert.-butylamino propane maleinate | 25.0 |
| corn starch | 175.0 |
| | 200.0 |

The ingredients are intensively admixed and 200 mg portions of the mixtures are filled into gelatin capsules of suitable size. Each capsule contains 25 mg of the optically active substance.

| EXAMPLE C - INJECTABLE SOLUTION | | |
|---|---|---|
| | | parts |
| 1-(2-methyl-4-cyanophenoxy)-2-hydroxy-3-tert.-butylamino-propane hydrochloride | | 2.5 |
| sodium salt of EDTA (ethylenediaminetetraacetic acid) | | 0.2 |
| distilled water | ad. | 100.0 |

Preparation

The active substance and the EDTA-salt were dissolved in sufficient water and distilled water to the desired volume was added. The solution was filtered free of suspended particles and filled into 1 cm-ampules under aseptic conditions. Then, the ampules were sterilized and sealed so that each of these ampules contained 25 mg of active substance.

EXAMPLE D - SUSTAINED RELEASE TABLETS

|   |   | gm |
|---|---|---|
| 1. | 1-(2-cyano-3-methyl-phenoxy)-2-hydroxy-3-tert.-butylamino-propane hydrochloride | 25.0 |
|   | carboxymethylcellulose (CMC) | 295.0 |
|   | stearic acid | 20.0 |
|   | cellulose acetate phthalate (CAP) | 40.0 |
|   |   | 380.0 |
| 2. | 1-(2-cyanophenoxy)-2-hydroxy-3-tert.-butylamino-propane . HCl | 40.0 |
|   | carboxymethylcellulose (CMC) | 300.0 |
|   | stearic acid | 20.0 |
|   | cellulose acetate phthalate | 40.0 |
|   |   | 400.0 |

The active substance, the carboxymethylcellulose and the stearic acid are intensively admixed and the mixture is granulated in the usual manner, a solution of the cellulose acetate phthalate in 200 ml of a mixture of ethanol and ethylacetate is used for this purpose. The granulate is then compressed into 380 mg kernels, which are in the usual manner coated with a sugar containing 5% solution of polyvinylpyrrolidone in water. Each tablet contains 25 mg of active ingredients.

PHARMACOLOGICAL DATA

The compounds of the invention were tested for β-adrenergic blocking activity in adult laboratory guinea pigs under urethane anaesthesia.

The bradycardia activity of the compounds was determined by administering the test compounds by intravenous injection at 5 progressively increasing dosages (0.1 mg/kg, 0.3 mg/kg, 1 mg/kg, 3 mg/kg and 10 mg/kg for each compound) to 4 animals per compound and ascertaining the decrease of the basic frequency of the heart beat by means of an electrical recorder.

After each determination of the decrease of the basic frequency, 1μ/kg of isoproterenol [ = α (isopropylaminomethyl) protocatechuyl alcohol] was administered to the same animal by intravenous injection, and the maximum frequency change was determined.

The results of both determinations (bradycardia activity and isoproterenol antagonistic activity) were plotted as a doseactivity curve, and the curve for each compound was compared with a corresponding curve for the standard control compound dichlorisoproterenol (DCI), a known effective β-adrenergic blocking agent. The following results were obtained.

TABLE I

| Compound | Bradycardia Activity | Isoproterenol-Antagonistic Activity |
|---|---|---|
| 1-(2-methoxy-5-cyanophenoxy)-2-hydroxy-3-tert.-butylamino propane . HCl | 6.5 × DCI | 10.9 × DCI |
| 1-(2-cyano-3-methylphenoxy)-2-hydroxy-3-tert.-butylamino propane . HCl | 10 × DCI | 60 × DCI |
| 1-(2-methyl-4-cyanophenoxy)-2-hydroxy-3-tert.-butylamino propane . HCl | 43 × DCI | 33 × DCI |
| 1-(2,4-dichloro-3-aminophenoxy)-2-hydroxy-3-tert.-butylamino-propane . 2 HCl | 59 × DCI | 63 × DCI |

Various modifications of the compositions and method of the invention may be made without departing from the spirit or scope thereof and it is to be understood that the invention is to be limited only as defined in the appended claims.

We claim:

1. A composition having bradycardia and isoproterenol antagonistic activity comprising a small but effective amount of at least one active compound selected from the group consisting of racemates of 1-phenoxy-2-hydroxy-3-tert.-butylamino propanes of the formula

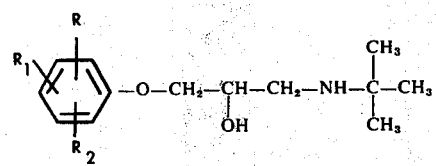

wherein R is COOR' where R' is alkyl of 1 to 4 carbon atoms; $R_1$ is selected from the group consisting of hydrogen, alkoxy and alkylthio of 1 to 4 carbon atoms and alkenyl and alkynyl of 2 to 4 carbon atoms and $R_2$ is selected from the group consisting of hydrogen, halogen and alkyl and alkoxyl of 1 to 4 carbon atoms, their optically active isomers and their non-toxic, pharmaceutically acceptable acid addition salts of said racemates and said optically active isomers and a major amount of a pharmaceutical carrier.

2. A composition of claim 1 wherein the amount of active ingredient is 1 to 300 mg.

3. A composition of claim 1 wherein $R_1$ is hydrogen.

4. A composition of claim 1 wherein the active compound is 1-(2-methoxy-carbonylphenoxy)-2-hydroxy-3-tert.-butylamino propane and its non-toxic, pharmaceutically acceptable acid addition salts.

5. A composition of claim 1 wherein the active compound is 1-(4-methoxy-carbonylphenoxy)-2-hydroxy-3-tert.-butylamino propane and its non-toxic, pharmaceutically acceptable acid addition salts.

6. A composition of claim 1 wherein the active compound is 1-(2-chloro-4-methoxycarbonylphenoxy)-2-hydroxy-3-tert.-butylamino propane and its non-toxic, pharmaceutically acceptable acid addition salts.

7. A method of producing bradycardia and suppressing tachycardiac effects of N-isopropyl-noradrenaline in warm-blooded animals which comprises administering to warm-blooded animals a safe and effective amount of at least one compound selected from the group consisting of racemates of 1-phenoxy-3-hydroxy-3-tert.-butylamino propanes of the formula

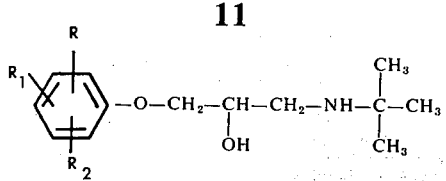

wherein R is COOR' where R' is alkyl of 1 to 4 carbon atoms; $R_1$ is selected from the group consisting of hydrogen, alkoxy and alkylthio of 1 to 4 carbon atoms and alkenyl and alkynyl of 2 to 4 carbon atoms and $R_2$ is selected from the group consisting of hydrogen, halogen and alkyl and alkoxy of 1 to 4 carbon atoms, their optically active isomers and their non-toxic, pharmaceutically acceptable acid addition salts of said racemates and said optically active isomers.

8. The method of claim 7 wherein the active compound is 1-(2-methoxycarbonylphenoxy)-2-hydroxy-3-tert.-butylamino propane or its non-toxic, pharmaceutically acceptable acid addition salts.

9. The method of claim 7 wherein the active compound is 1-(4-methoxycarbonylphenoxy)-2-hydroxy-3-tert.-butylamino propane or its non-toxic, pharmaceutically acceptable acid addition salts.

10. The method of claim 7 wherein the active compound is 1-(2-chloro-4-methoxycarbonylphenoxy)-2-hydroxy-3-tert.-butylamino propane or its non-toxic, pharmaceutically acceptable acid addition salts.

* * * * *